(12) United States Patent
Massaro

(10) Patent No.: US 6,637,476 B2
(45) Date of Patent: Oct. 28, 2003

(54) ROBOTICALLY MANIPULABLE SAMPLE HANDLING TOOL

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 0 days.

(21) Appl. No.: 10/113,865

(22) Filed: Apr. 1, 2002

(65) Prior Publication Data

US 2003/0183301 A1 Oct. 2, 2003

(51) Int. Cl.$^7$ ................................................ B65B 1/04
(52) U.S. Cl. ...................... 141/237; 141/1; 141/130; 422/100; 422/101; 422/102
(58) Field of Search .................... 141/1, 130, 237; 422/100, 101, 102; 73/864.24, 863.1, 863.32

(56) References Cited

U.S. PATENT DOCUMENTS

| | | | |
|---|---|---|---|
| 3,568,735 A | * | 3/1971 | Lancaster .................... 422/100 |
| 3,744,376 A | | 7/1973 | Carpenter |
| 3,782,682 A | | 1/1974 | Lale |
| 3,881,846 A | | 5/1975 | Kashmerick |
| 3,934,611 A | | 1/1976 | Gachot et al. |
| 4,119,120 A | | 10/1978 | Mehaffy et al. |
| 4,148,334 A | | 4/1979 | Richards |
| 4,262,711 A | | 4/1981 | Anderson |
| 4,274,452 A | | 6/1981 | Schmitt |
| 4,283,008 A | | 8/1981 | Ring, Jr. |
| 4,304,257 A | | 12/1981 | Webster |
| 4,451,023 A | | 5/1984 | Zakai |
| 4,532,805 A | | 8/1985 | Flesher |
| 4,771,204 A | | 9/1988 | Siegal |
| 4,824,072 A | | 4/1989 | Zakai |
| 4,844,872 A | | 7/1989 | Geiselman et al. |
| 4,848,722 A | | 7/1989 | Webster |
| 4,852,851 A | | 8/1989 | Webster |
| 4,858,883 A | | 8/1989 | Webster |
| 4,906,432 A | | 3/1990 | Geiselman |
| 4,925,153 A | | 5/1990 | Roomer |
| 5,083,742 A | | 1/1992 | Wylie et al. |
| 5,108,067 A | | 4/1992 | Straub |
| 5,154,693 A | | 10/1992 | East et al. |
| 5,176,359 A | | 1/1993 | Leveson et al. |
| 5,197,192 A | | 3/1993 | Wylie et al. |
| 5,203,368 A | | 4/1993 | Barstow et al. |
| 5,226,462 A | * | 7/1993 | Carl ........................... 141/130 |
| 5,254,311 A | * | 10/1993 | Ushikubo .................... 422/100 |
| 5,277,556 A | | 1/1994 | van Lintel |
| 5,343,909 A | | 9/1994 | Goodman |
| 5,496,009 A | | 3/1996 | Farrell et al. |
| 5,660,370 A | | 8/1997 | Webster |

(List continued on next page.)

FOREIGN PATENT DOCUMENTS

| | | |
|---|---|---|
| EP | 863 341 A1 | 9/1998 |
| WO | WO 98/03809 | 1/1998 |
| WO | WO 00/28215 | 5/2000 |
| WO | WO 01/01025 A2 | 1/2001 |
| WO | WO 01/66916 A2 | 9/2001 |

*Primary Examiner*—Gregory Huson
*Assistant Examiner*—Khoa Huynh
(74) *Attorney, Agent, or Firm*—Wolf, Greenfield & Sacks, P.C.

(57) ABSTRACT

A robotically manipulable sample handling tool, such as a colony picking head or robotic pipetting tool, includes needles arranged on the tool. Actuators may be associated with each needle to control flow for the needle, e.g., to move the needle and/or draw fluid into/expel fluid from the needle. The actuators may be arranged so that needles are individually controlled by a controller that outputs a number of control signals that is less than the total number of needles. The actuators may be membrane valves that receive two signals from a controller; a first signal that opens or closes the valve, and a second signal that causes fluid flow through the valve to actuate a needle.

26 Claims, 3 Drawing Sheets

U.S. PATENT DOCUMENTS

| | | | |
|---|---|---|---|
| 5,660,728 A | | 8/1997 | Saaski et al. |
| 5,660,792 A | * | 8/1997 | Koike .................. 422/101 |
| 5,697,153 A | | 12/1997 | Saaski et al. |
| 5,743,295 A | | 4/1998 | Alcock et al. |
| 5,758,863 A | | 6/1998 | Buffet et al. |
| 5,775,371 A | | 7/1998 | Pan et al. |
| 5,791,375 A | | 8/1998 | Pan et al. |
| 5,794,641 A | | 8/1998 | Pan et al. |
| 5,834,314 A | | 11/1998 | Gates et al. |
| 5,836,750 A | | 11/1998 | Cabuz |
| 5,839,467 A | | 11/1998 | Saaski et al. |
| 5,910,244 A | | 6/1999 | Stamos et al. |
| 5,941,501 A | | 8/1999 | Biegelsen et al. |
| 5,967,163 A | | 10/1999 | Pan et al. |
| 5,971,355 A | | 10/1999 | Biegelsen et al. |
| 6,007,046 A | | 12/1999 | Rothermel |
| 6,012,902 A | | 1/2000 | Parce |
| 6,033,911 A | * | 3/2000 | Schultz et al. ............ 422/100 |
| 6,039,211 A | * | 3/2000 | Slater et al. ............ 141/130 |
| 6,044,876 A | * | 4/2000 | Ally et al. ............ 141/130 |
| 6,068,978 A | | 5/2000 | Zaun et al. |
| 6,074,611 A | | 6/2000 | Flesher |
| 6,089,534 A | | 7/2000 | Biegelsen et al. |
| 6,106,245 A | | 8/2000 | Cabuz |
| 6,123,316 A | | 9/2000 | Biegelsen et al. |
| 6,158,712 A | | 12/2000 | Craig |
| 6,176,399 B1 | | 1/2001 | Schantz et al. |
| 6,202,687 B1 | | 3/2001 | Park |
| 6,240,944 B1 | | 6/2001 | Ohnstein et al. |
| 6,244,119 B1 | | 6/2001 | Theran |
| 6,257,268 B1 | | 7/2001 | Hope et al. |
| 6,299,028 B1 | | 10/2001 | Iizuka et al. |
| 6,416,718 B1 | * | 7/2002 | Maiefski et al. ............ 422/103 |
| 6,506,611 B2 | * | 1/2003 | Bienert et al. ............ 422/100 |
| 2001/0019845 A1 | | 9/2001 | Bienert et al. |
| 2001/0036424 A1 | | 11/2001 | Takahashi et al. |

* cited by examiner

ROBOTICALLY MANIPULABLE SAMPLE HANDLING TOOL

BACKGROUND OF THE INVENTION

1. Field of Invention

This invention relates to robotically manipulable sample handling tools, such as robotic pipetting devices.

2. Related Art

Robotically manipulated tools having a plurality of picking needles are widely used, for example, in proteomic and genomic research. These devices are used to move material samples both to and from a variety of different work areas, such as microtiter trays, gels having separated DNA fragments, and other material holding devices. Some such tools may have a plurality of needles arranged in an array that corresponds to wells in a microtiter tray, such as the commonly-known 96-well or 384-well plate. The array of needles arranged to correspond with all of the wells in a microtiter tray may allow material to be simultaneously deposited in, and removed from, wells in the microtiter tray, thus increasing the speed at which a plurality of samples in a microtiter tray may be processed.

Many sample handling tools are arranged so that all of the needles on the tool may be simultaneously actuated, e.g., so material may be simultaneously deposited in all wells of a tray. While this arrangement can provide rapid handling of multiple samples, it does not allow for individualized handling for selected wells in a tray. Other handling tools provide for individual actuation of needles on a tool, but require that a controller for the tool be capable of outputting an individual control signal for each needle actuator. The inventor has appreciated that providing individual control signals for each needle can be cumbersome. For example, a sample handling tool having 96 needles would require at least 96 control signal leads to provide a control signal for each needle.

SUMMARY OF THE INVENTION

Aspects of the invention provide a sample handling tool that allows for individual control of needles on the tool without requiring a controller to output individual control signals for each of the needles. In one embodiment, needles and their corresponding actuators may be grouped into control groups so that actuators in a control group receive a same control signal from a controller, e.g., to enable the actuators to activate a corresponding needle. The needles and actuators may also be grouped into drive groups so actuators in a drive group receive a same drive signal from the controller, e.g., to activate a needle. Actuators receiving both a control signal to enable the actuator and a drive signal to actuate the needle will, in fact, actuate the needle. The groups may be arranged so that control groups have only one actuator/needle in common with drive groups. As a result, an individual needle may be actuated by a controller by providing an appropriate control signal to the needle's control group and an appropriate drive signal to the needle's drive group. Since the control and drive groups have only the one needle in common, only the one needle on the tool may receive both an appropriate control and drive signal, thereby actuating the needle.

In one illustrative embodiment in accordance with the invention, a robotically manipulable material handling tool includes a tool body and a plurality of needles mounted to the tool body. Each of the plurality of needles is constructed and arranged to remove material from a work area and deposit material on a work area. The tool also includes a plurality of actuators with each of the plurality of actuators associated with a corresponding one of the plurality of needles. The actuators are constructed and arranged to actuate a corresponding needle and are grouped into a first member of control groups and a second number of drive groups, with each control group and drive group having only one actuator in common. A plurality of control switches are mounted to the tool body with each of the plurality of control switches associated with a corresponding control group of actuators and adapted to provide a control signal to actuators in the corresponding control group. A plurality of drive switches are mounted to the body with each of the drives switches associated with a corresponding drive group and adapted to provided a drive signal to the actuators in the corresponding drive group. The plurality of control switches and drive switches are constructed and arranged to provide control signals and drive signals, respectively, to individually actuate each of the plurality of needles.

In another illustrative embodiment, a robotically manipulable material handling tool includes a tool body and a first number of needles mounted to the tool body. Each of the needles is constructed and arranged to remove material from a work area and deposit material on a work area. A first number of membrane valves are each associated with a corresponding needle and control flow for the needle. A valve controller is constructed and arranged to control each of the membrane valves by providing a maximum of a second number of signals to the membrane valves, where the second number is less than the first number. The valve controller is adapted to control the membrane valves to individually control flow for each needle.

In another illustrative embodiment, a robotically manipulable material handling tool includes a tool;body and a first number of needles mounted to the tool body. Each of the needles is constructed and arranged to remove material from a work area and deposit material on a work area. The tool also includes a first number of actuators with each actuator associated with a corresponding needle and constructed and arranged to cause the corresponding needle to move relative to the tool body. A controller is mounted to the tool body and constructed and arranged to control each of the actuators by providing a maximum of a second number of signals to the actuators where the second number is less than the first number. The controller is adapted to control the actuators and individually move needles relative to the tool body and/or simultaneously move a plurality of needles relative to the tool body.

In another illustrative embodiment, a robotically manipulable material handling tool includes a tool body and a plurality of needles mounted to the tool body in M columns and N rows. Each of the needles is constructed and arranged to remove material from a work area and deposit material on a work area. A plurality of addressing valves are each associated with a corresponding needle and control flow for the needle. A plurality of switches provides signals to the addressing valves and the number of switches is equal to M+N. The plurality of switches are adapted to provide signals to the addressing valves to individually control flow for each needle.

In another illustrative embodiment, a robotically manipulable material handling tool includes a tool body and a plurality of needles mounted to the tool body in M columns and N rows. Each of the needles is constructed and arranged to remove material from a work area and deposit material on a work area. A plurality of membrane valves are each associated with a corresponding needle and control flow for the needle to move the needle and/or cause fluid to move in the needle. A plurality of control valves provide fluid control signals to the membrane valves with each control valve associated with the corresponding column of needles and providing a fluid control signal to control the membrane valves corresponding to the column of needles between open and closed states. A plurality of drive valves provide fluid drive signals to the membrane valves with each drive valve associated with a corresponding row of needles and providing a fluid drive signal to either move needles and/or cause fluid to move in needles in the corresponding row. The number of control and drive valves is equal to M+N and the control and drive valves are adapted to provide signals to the membrane valves to individually control either movement of and/or flow in each needle.

BRIEF DESCRIPTION OF THE DRAWINGS

Illustrative embodiments in accordance with the invention are described below with reference to the following drawings, in which like numerals reference like elements, and wherein.

DETAILED DESCRIPTION

Various aspects of the invention are described below with reference to illustrative embodiments. However, it should be understood that the invention is not limited to those embodiments described below, but instead may be used in any suitable system or arrangement.

In one aspect of the invention, needles in a robotic sample handling tool may be individually actuated or otherwise controlled by a controller on the tool by outputting a maximum number of signals that is less than the total number of needles on the tool. For example, if the tool has an M×N array of needles, the controller may be arranged to output a maximum of M+N signals, yet still be capable of individually actuating selected needles. Such actuation may include moving a needle relative to the tool, such as extending the needle away from the tool apart from other needles on the body, controlling flow in the needle, such as drawing fluid into or expelling fluid out from the needle, or otherwise causing the needle to perform one or more material handling functions. In addition, the controller may simultaneously actuate all needles in the array, or simultaneously actuate selected groups of needles, such as all or selected needles in a particular row or column of needles. This arrangement may allow individual control of needles without requiring a controller to output an individual control signal for each needle.

In one aspect of the invention, actuators in a material handling tool may be grouped into control groups and drive groups, where each control group has one actuator in common with each drive group. Actuators in a control group may be linked so that a common control signal may be simultaneously provided to all actuators in the control group, e.g., to cause the actuators to be in an enable state ready to actuate a corresponding needle. Actuators may also be linked so that a common drive signal may be simultaneously provided to all actuators in a drive group, where the drive signal causes actuation of a needle when received by an actuator in an enable state. Since control groups and drive groups include one actuator in common, a particular needle may be actuated by providing a control signal to the needle's control group and providing a drive signal to the needle's drive group. That is, a needle may be actuated only when its corresponding actuator receives both an appropriate control signal and an appropriate drive signal. Accordingly, individual actuation of needles can be effected by a controller without requiring the controller to output control signals for each needle. Instead, the controller may be arranged to output a maximum number of control signals that is less than the number of needles, e.g., equal to the total number of control and drive groups. Such an arrangement also allows for simultaneous actuation of all needles in the tool, or selected groups of needles.

Figure 1:
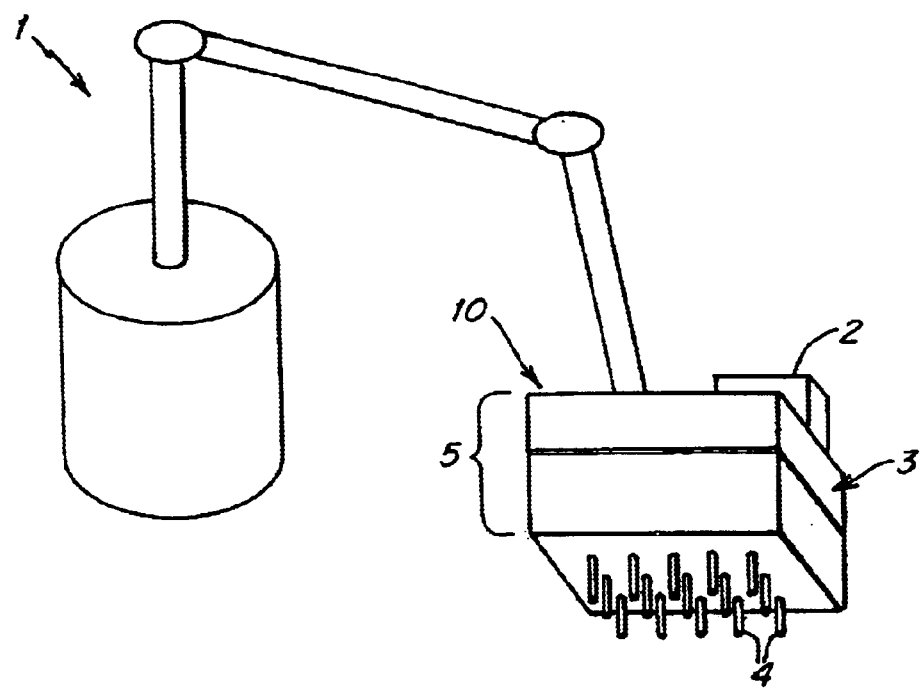
FIG. 1 is a schematic diagram of a robotically manipulated tool in accordance with the invention.

FIG. 1 is a schematic diagram of a robot 1 manipulating a material handling tool 10 in accordance with the invention. The robot 1 may move the material handling tool 10 and allow needles 4 on the tool 10 to pick up and/or deposit material on one or more work areas, such as microtiter trays, gels containing separated DNA fragments or other biologic materials, etc. For example, the robot 1 may move the tool 10 so that one or more needles 4 are appropriately positioned with respect to a microtiter tray and then actuate one or more needles 4 to remove material from, or deposit material in, wells in the microtiter tray. Those of skill in the art will understand that the needles may be actuated to perform other material handling operations, such as colony or plaque picking at the direction of a machine vision system. The purposes and methods for such material handling are well known to those in the art and not described in detail herein.

Although the robot 1 is shown in FIG. 1 as having a base and an articulated arm, the robot 1 may be of any suitable type or construction and may be capable of moving the tool 10 in any suitable number of degrees of freedom. For example, the robot may be a gantry-type robot capable of moving the tool 10 in three degrees of freedom. Of course, other suitable robotic configurations capable of moving the tool 10 in one or more degrees of freedom may be used. The tool 10 and robot 1 may include a coupling to allow the robot 1 to exchange the tool 10 for other tools, thereby allowing the robot 1 to perform automated operations with different tools. The robot 1 or system controller may include a vision system or other suitable device to control positioning of needles 4 with respect to target areas, as is well known. In addition, a connection between the tool 10 and the robot 1 may provide physical support to the tool 10 as well as provide electrical power, control signals, a fluid supply or other fluid signal, etc. As used herein, "fluid" refers to gases and/or liquids.

In the illustrative embodiment of FIG. 1, the tool 10 includes a controller 2 that outputs signals to actuators 3 that cause corresponding needles 4 to be actuated. As discussed above, actuation of a needle 4 may cause the needle 4 to move relative to the tool 10, such as extend away from the tool to pick or place material on a work area, control flow in the needle, such as drawing fluid into or expelling fluid out from the needle, or otherwise cause the needle to perform one or more material handling functions. In this illustrative embodiment, the controller 2, actuators 3 and needles 4 are all mounted to a body 5 of the tool 10. Although.in this illustrative embodiment the body 5 has a box-like shape, the body 5 may be arranged in any suitable way. Further, the needles 4 in this illustrative embodiment are arranged in a 3×4 array and extend from a bottom of the body 5, but any suitable number of needles 4 may be arranged in any suitable way on the body 5, e.g., to accommodate particular well patterns in a microtiter tray. The needles 4 may be arranged to receive removable pipette tips or other devices to handle materials, or may be arranged to handle materials directly.

The controller 2, which may in some embodiments be provided off of the tool 10, may provide any suitable signal or combination of signals to the actuators 3 to actuate the needles 4. For example, the controller 2 may provide electrical signals, magnetic signals, optical signals, fluid signals (e.g., changes in fluid pressure and/or flow), or combinations of such signals, such as providing both an electrical signal and a fluid signal to the actuators 3. Typically, signals provided by the controller 2 will depend upon the type of actuators 3. For example, the actuators 3 may be pneumatically-controlled fluid valves that open, close or otherwise change state based on a fluid signal.

Of course, the actuators may include electrically-controlled fluid valves, relays, or other suitable devices to actuate a corresponding needle. For example, the tool 10 may include one actuator for each needle, where each actuator includes a valve and associated pneumatic ram such that when the valve is open and air pressure is supplied through the open valve, the pneumatic ram may extend, and thereby extend a corresponding needle 4 from the body 5. Thus, the actuators may be responsive to two signals received from the controller 2 to actuate the needles 4. Having the actuators 3 respond to two signals from the controller 2 may allow for matrix-type addressing of the actuators 3, as discussed in more detail below.

The controller 2 may operate autonomously to actuate the needles 4 or operate at the direction of a higher level controller that is part of a material handling system. For example, the controller 2 may receive a signal to activate a particular needle or group of needles at a particular time and/or position of the tool 10, and generate and output appropriate signals to cause the desired actuation. The controller 2 may receive the signals in any suitable way, such as by wired and/or wireless link, and in any suitable format and/or communications protocol. The controller 2 and/or higher level controller may include any suitable general purpose data processing system, which can be, or include, a suitably programmed general purpose computer, or network of general purpose computers, and other associated devices, including communication devices, and/or other circuitry or components necessary to perform the desired input/output or other functions. The controllers can also be implemented at least in part as single special purpose integrated circuits (e.g., ASICs), or an array of ASICs, each having a main or central processor section for overall, system-level control and separate sections dedicated to performing various different specific computations, functions and other processes under the control of the central processor section. The controllers can also be implemented using a plurality of separate dedicated programmable integrated or other electronic circuits or devices, e.g., hardwired electronic or logic circuits, such as discrete element circuits or programmable logic devices. The controllers may also include other devices, such as an information display device, user input devices, such as a keyboard, user pointing device, touch screen or other user interface, data storage devices, communication devices or other electronic circuitry or components.

Figure 2:
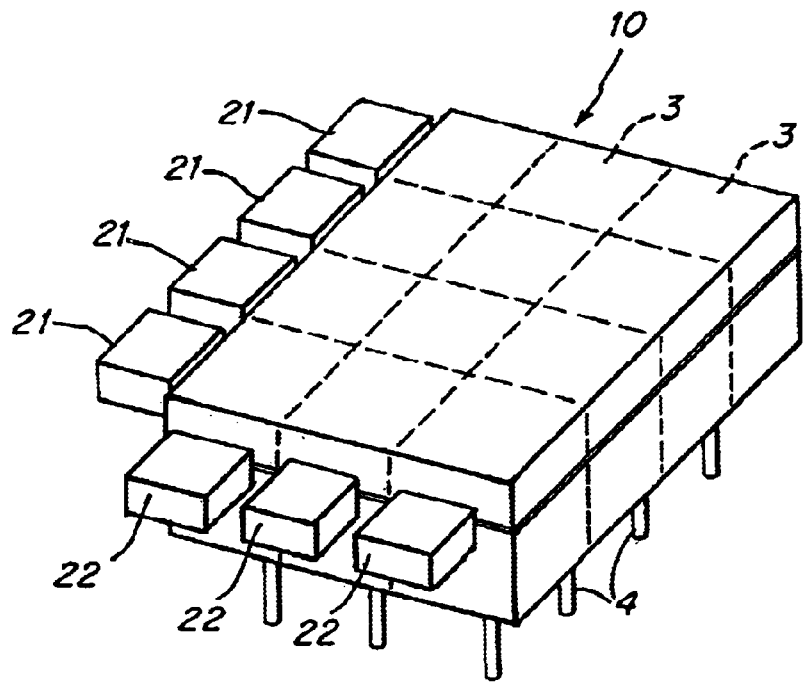
FIG. 2 is a schematic, perspective view of a tool in accordance with the invention.

FIG. 2 shows a perspective view of a tool 10 in accordance with the invention. In this illustrative embodiment, the tool 10 includes a 3×4 array of actuators 3 that are each associated with a corresponding needle 4. Thus, when an actuator 3 receives appropriate signals, the corresponding needle 4 is actuated, e.g., fluid flow in the needle is controlled and/or the needle 4 is moved relative to the body 5. In this illustrative embodiment, the controller 2 includes four control switches 21 that are associated with actuators 3 in rows across the tool 10, and drive switches 22 that are associated with actuators 3 in columns on the tool 10. Control signals may be provided to the control switches 21 and drive switches 22 by a portion of the controller 2 (e.g., a data processor and associated memory) on the tool 10, or by another source off of the tool 10. Based on these control signals, the control switches 21 and drive switches 22 may provide suitable signals to the actuators 3 to actuate a particular needle or needles. The switches 21 and 22 may be any suitable device capable of responding to a control signal and providing a signal to corresponding actuators 3. For example, the switches 21 and 22 may include electrically-controlled valves capable of switching an associated control or drive line 23 or 24 between one or more fluid lines, e.g., sources of relatively high or low pressure, or sources of fluid flow. Pressure or other fluid flow sources may be provided to the switches 21 and 22 by lines (not shown) that lead to a pump, metering piston or other devices off of the tool body 10.

It should be understood that although the actuators 3 in this illustrative embodiment are arranged in columns and rows, the actuators 3 may be logically grouped in any suitable way and in any suitable pattern. Further, the tool 10 is not limited to a 3×4 array, but instead may have any suitable number of actuators and/or needles arranged in any suitable pattern, such as a pattern that allows the needles 4 to interact with standard 96-well, 384-well or other size/configuration microtiter trays or other material sample holders. Thus, the 3×4 array in this illustrative embodiment is used for simplicity and ease of reference, but should in no way be interpreted as limiting aspects of the invention in any way.

Figure 3:
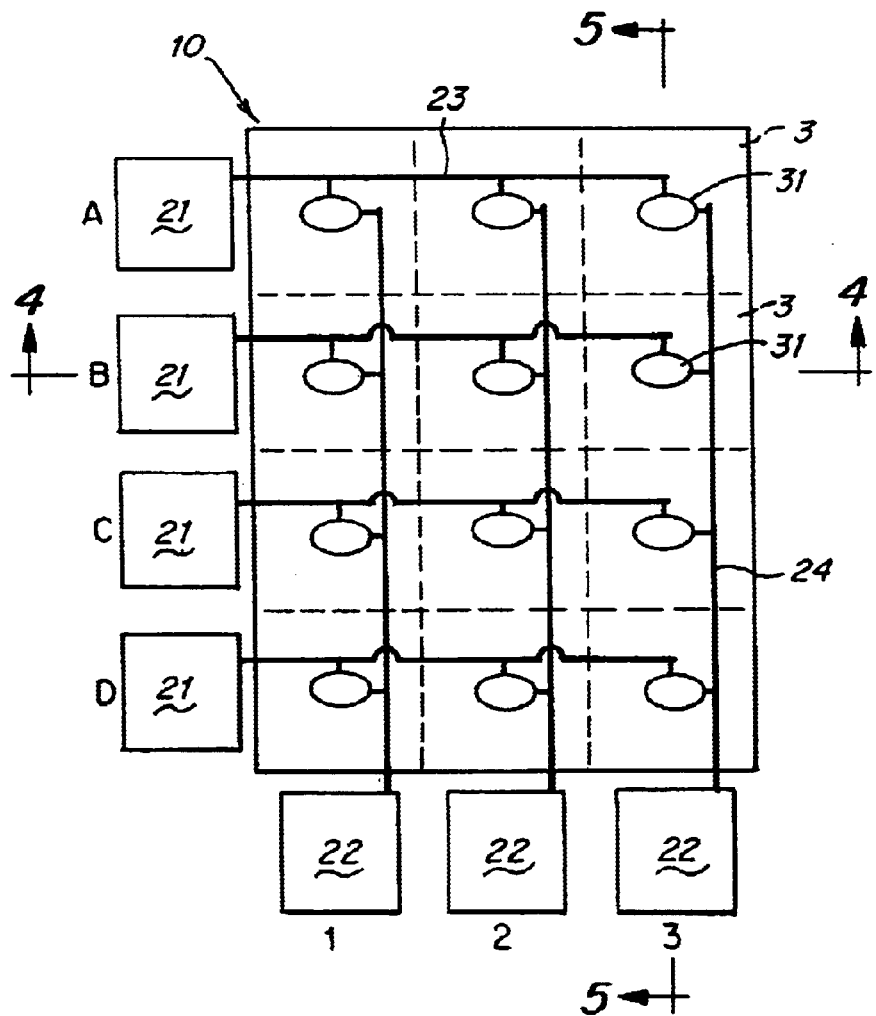
FIG. 3 is a plan view of the tool shown in FIG. 2 and illustrates how individual needle actuators may be addressed.

FIG. 3 shows a schematic top view of the tool 10 shown in FIG. 2. Rows of actuators 3 are labeled A–D, and one control switch 21 may correspond to each row A–D. Similarly, columns of the actuators 3 are numbered 1–3 and one drive switch 22 may correspond to each column 1–3. In this illustrative embodiment, each control switch 21 provides a control signal approximately simultaneously to all actuators 3 in the corresponding row via a control line 23. Thus, control groups of actuators 3 in this embodiment are arranged in rows. The control signal provided to a control group may cause the actuators 3 in the group to change state between an enable state and a disable state. In the disable state, an actuator 3 may be unable to actuate a corresponding needle 4. In the enable state, the actuator 3 may be free to actuate the corresponding needle 4 upon receipt of an appropriate drive signal. Each of the drive switches 22 may approximately simultaneously provide a drive signal to all actuators 3 in a corresponding column along a drive line 24. Thus, drive groups in this embodiment are arranged in columns. The drive signal may cause actuators in an enable state to actuate a corresponding needle 4. However, in this embodiment, an actuator in a disable state may not actuate a corresponding needle even if a drive signal that would otherwise cause actuation is received. Accordingly, individual actuators may be caused to actuate a corresponding needle 4, i.e., individual actuators 3 may be addressed, by providing a control signal along the actuator's corresponding control line 23 and a drive signal along the actuator's corresponding drive line 24. For example, the actuator 3 in the top right corner of the tool 10 as shown in FIG. 3 may be addressed by providing a control signal from the control switch 21 for row A and providing a drive signal from the drive switch 22 for column 3. Other actuators in the row A and in column 3 will not actuate a corresponding needle 4 unless an appropriate control signal and drive signal are received along appropriate lines. Thus, when the actuator 3 in the top right corner of the tool 10 (i.e., position A-3) is actuated, actuators in the row A and in columns 1 and 2 will not be actuated unless drive signals are provided by the drive switches 22 for columns 1 and 2. As a result, individual needles 4 may be actuated by providing appropriate signals to groups, e.g., rows and/or columns, of actuators in the tool 10.

It should also be appreciated that selected groups of actuators 3 may be addressed by providing appropriate signals along the rows A–D and columns 1–3. For example, all needles on the tool 10, or selected needles in a particular row or column may be approximately simultaneously actuated, e.g., all of the actuators 3 in row A may be actuated by providing an appropriate control signal from the control switch 21 for row A and appropriate drive signals from the drive switches 22 for columns 1–3. It will be appreciated that other selected groups of needles may be approximately simultaneously actuated by providing signals on appropriate control and drive lines 23 and 24.

Figure 4:
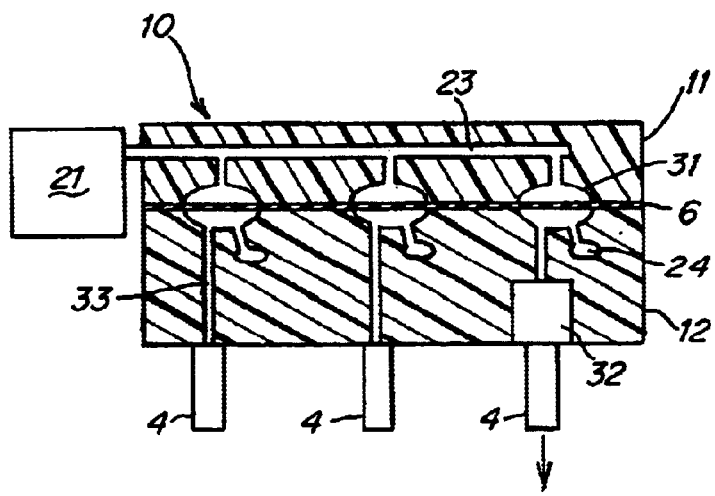
FIG. 4 is a cross-sectional view along the line 4—4 in FIG. 3.
Figure 5:
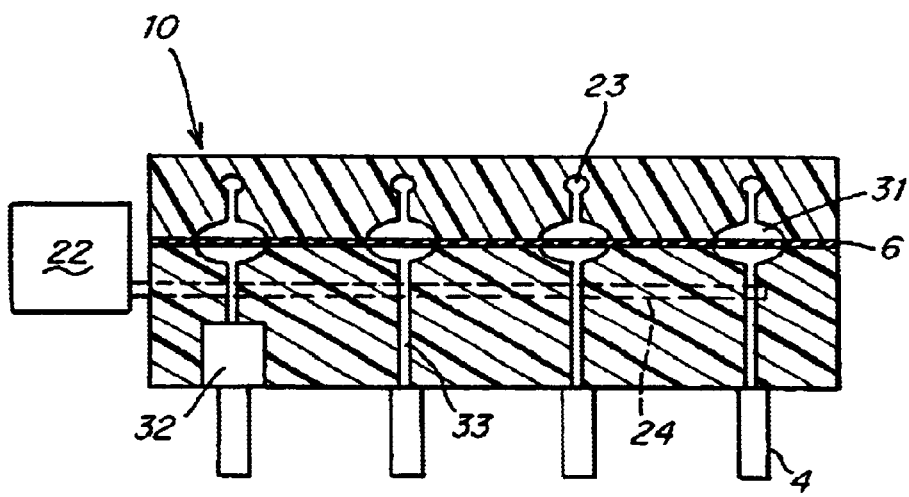
FIG. 5 is a cross-sectional view along the line 5—5 in FIG. 3.

FIG. 4 shows a cross-sectional view of the tool 10 along the line 4—4 in FIG. 3, and FIG. 5 shows a cross-sectional view of the tool 10 along the line 5—5 in FIG. 3. As discussed above, the actuators 3 may take any suitable form, but in this illustrative embodiment, include one or more membrane valves 31. The various control lines 23, drive lines 24, needle channels 33, chambers for valves 31 and other features are formed in upper and lower blocks 11 and 12 of the tool body 10. The blocks 11 and 12 may be made of any suitable material(s), such as plastic, and the channels, lines, chambers and other features may be formed in any suitable way using any suitable process. For example, each block may be made of multiple layers of plastic material that have grooves or channels or are otherwise formed to create the desired lines, channels, etc. in the tool body 10. These layers may be joined together, e.g., by heating the layers and pressing them together, to form a unitary block. The membrane valves 31 may be formed by positioning a flexible member 6, such as a sheet of silicone rubber, between the blocks 11 and 12 and securing the blocks 11 and 12 together. The construction of membrane valves is well known, and alternate methods of construction will be appreciated by those of skill in the art.

Figure 6:
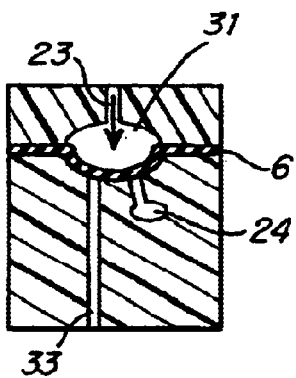
FIG. 6 is a schematic view of a valve that controls actuation of a corresponding needle in a closed state.
Figure 7:
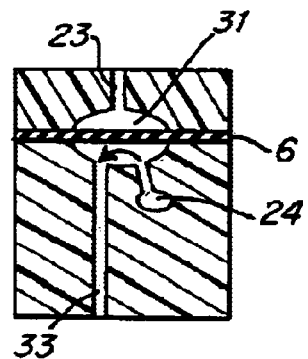
FIG. 7 is a schematic view of the FIG. 6 valve in an open state.

In this embodiment, the membrane valves 31 operate based on a control signal provided along a corresponding control line 23. For example, as shown in FIG. 6, when a relatively high pressure exists in the control line 23, portions of a flexible member 6 in the membrane valves 31 in communication with the control line 23 flex downward toward a bottom portion of the valve chamber to block flow from a drive line 24 to a needle channel 33. As shown in FIG. 7, release of the pressure in the control line 23 may allow the flexible member 6 to return to its rest state to allow flow from the drive line 24 to the needle channel 33. Switching of the control signal is performed by the control switch 21, which may include a valve or other arrangement that selectively switches the control line 23 between a source of high pressure and ambient or relatively lower pressure to control the valves 31 along the control line 23.

FIGS. 4 and 5 show that rows of valves 31 may be connected to a common control line 23, and columns of valves 31 may be connected to a common drive line 24. Signals provided on the control lines 23 in this embodiment serve to switch the valves 31 between an open (or enable) state and closed (or disable) state. When a valve is in an enable state, a drive signal provided along the valve's drive line 24 may be provided through the valve 31 to an associated needle channel 33. Therefore, a control signal may be provided to valves 31 in a row to switch the valves to an enable state, and a drive signal supplied to a drive line 24 for the valves 31 in an enable state may cause actuation of needles corresponding to the enabled valves 31. For example, when a valve is in an enable state, fluid may flow through the valve to draw fluids into, or expel fluids out of, a needle 4. Alternately, the drive signal, such as a pressurized fluid flow through the valve 31, may cause a pneumatic ram 32 or other device to move an associated needle 4, e.g., extend the needle away from the tool 10 to pick material from a work area as shown in FIG. 4. Thus, in one illustrative embodiment, actuators 3 in a tool 10 may include a membrane valve or other similar device to control fluid flow in a needle 4, or may include a membrane valve and pneumatic ram to control movement of an associated needle 4.

The control and drive signals may also cause the membrane valves 31 to perfomn other actuation operations with respect to the needles, such as pumping fluid through a corresponding needle channel 33 and/or drawing or expelling a metered amount of fluid into or out of a corresponding needle 4. Pumping and metering operations may be performed by, for example, moving the flexible member in a valve 31 to a closed state, closing a drive line 24 for the valve 31 at a drive switch 22, and moving the flexible member in the valve 31 to an open state, thereby causing fluid to be drawn into the needle 4. Movement of the flexible member 6 may be closely controlled to perform accurate fluid metering through the valve's needle, e.g., by controlling the amount of fluid drawn from the valve by the control line 23. Such control can be performed by a metering piston coupled to the control line 23 or drive line 24, by accurately timing the opening and closing of a valve in the control switch 21 while supplying a constant fluid flow through the valve 31, or other means as will be appreciated by those of skill in the art.

It should be appreciated that although the control and drive switches in this illustrative embodiment control fluid flow to corresponding rows and columns of valves, the switches may provide other signal types to the actuators, such as electrical, optical, magnetic and other signal types. Similarly, the actuators and/or valves 31 in this embodiment may include or be replaced with any other suitable element (s), such as electrical or optical relays, transistors, optical valves, etc., and the actuators 3 may include other drive elements, such as hydraulic rams, solenoid actuators, motors, and so on. Therefore, any suitable arrangement of elements may be used as actuators to receive control and drive signals and actuate a corresponding needle.

While the invention has been described with reference to various illustrative embodiments, the invention is not limited to the embodiments described. Thus, it is evident that many alternatives, modifications, and variations of the embodiments described will be apparent to those skilled in the art. Accordingly, embodiments of the invention as set forth herein are intended to be illustrative, not limiting. Various changes may be made without departing from the invention.

What is claimed is:

1. A robotically manipulable material handling tool, comprising:
   a tool body;
   a plurality of needles mounted to the tool body, each of the plurality of needles constructed and arranged to remove material from a work area and deposit material on a work area;
   a plurality of actuators, each of the plurality of actuators associated with a corresponding one of the plurality of needles and constructed and arranged to actuate the corresponding needle, the plurality of actuators grouped into a first number of control groups and a second number of drive groups, each control group and drive group having two or more actuators, and each control group and drive group having only one actuator in common, the first and second numbers being greater than one;
   a plurality of control switches mounted to the tool body, each of the plurality of control switches associated with a corresponding control group of actuators and adapted to provide a control signal to the actuators in the corresponding control group of actuators; and
   a plurality of drive switches mounted to the tool body, each of the plurality of drive switches associated with a corresponding drive group and adapted to provide a drive signal to the actuators in the corresponding drive group;
   wherein the plurality of control switches and the plurality of drive switches are constructed and arranged to provide control signals and drive signals, respectively, to individually actuate each of the plurality of needles.

2. The tool of claim 1, wherein each of the plurality of actuators includes a membrane valve that controls fluid flow with respect to a corresponding needle.

3. The tool of claim 2, wherein each of the plurality of control switches includes a valve that provides an air pressure signal to membrane valves in a control group corresponding to the valve.

4. The tool of claim 2, wherein each of the plurality of drive switches includes a valve that provides a fluid flow to membrane valves in a drive group corresponding to the valve.

5. The tool of claim 2, wherein the plurality of needles and corresponding membrane valves are arranged in an M×N array with control groups of membrane valves arranged in rows and drive groups of membrane valves arranged in columns.

6. The tool of claim 5, wherein the plurality of control switches includes M valves that each provide an air pressure signal to membrane valves in a corresponding row.

7. The tool of claim 5, wherein the plurality of drive switches includes N valves that each provide a fluid flow to membrane valves in a corresponding column.

8. The tool of claim 5, wherein actuation of a needle includes extending the needle from the tool body.

9. The tool of claim 5, wherein actuation of a needle includes one of drawing fluid into and expelling fluid from the needle.

10. A robotically manipulable material handling tool, comprising:
    a tool body;
    a first number of needles mounted to the tool body, each of the needles constructed and arranged to remove material from: a work area and deposit material on a work area;
    a first number of membrane valves, each valve associated with a corresponding needle and controlling flow for the needle; and
    a valve controller constructed and arranged to control each of the membrane valves by providing a maximum of a second number of signals to the membrane valves, the second number being less than the first number;
    wherein the valve controller is adapted to control the membrane valves to individually actuate each needle.

11. The tool of claim 10, wherein the valve controller includes a plurality of first valves that each provide an air pressure signal to a corresponding group of membrane valves to control the membrane valves between open and closed states.

12. The tool of claim 11, wherein the valve controller includes a plurality of second valves that each provide a fluid flow to corresponding groups membrane valves.

13. The tool of claim 10, wherein the plurality of needles and corresponding membrane valves are arranged in an M×N array with control groups of membrane valves arranged in rows and drive groups of membrane valves arranged in columns.

14. The tool of claim 13, wherein the valve controller includes M valves that each provide an air pressure signal to membrane valves in a corresponding row.

15. The tool of claim 13, wherein the valve controller includes N valves that each provide a fluid flow to membrane valves in a corresponding column.

16. The tool of claim 13, wherein actuation of a needle includes extending the needle from the tool body.

17. The tool of claim 13, wherein actuation of a needle includes one of drawing fluid into and expelling fluid from the needle.

18. The tool of claim 13, wherein the valve controller is mounted to the tool body.

19. The tool of claim 10, wherein the valve controller is adapted to control the membrane valves to simultaneously control flow for a plurality of needles.

20. A robotically manipulable material handling tool, comprising:
    a tool body;
    a first number of needles mounted to the tool body, each of the needles constructed and arranged to remove material from a work area and deposit material on a work area;
    a first number of actuators, each actuator associated with a corresponding needle and constructed and arranged to cause the corresponding needle to move relative to the tool body; and
    a controller mounted to the tool body and constructed and arranged to control each of the actuators by providing a maximum of a second number of signals to the actuators, the second number being less than the first number;
    wherein the controller is adapted to control the actuators and individually move needles relative to the tool body, and the controller is adapted to control the actuators to simultaneously move a plurality of needles relative to the tool body.

21. A robotically manipulable material handling tool, comprising:

a tool body;

a plurality of needles mounted to the tool body in M columns and N rows, each of the needles constructed and arranged to remove material from a work area and deposit material on a work area;

a plurality of addressing valves, at least one addressing valve associated with a corresponding needle and controlling flow for the needle; and a plurality of switches that provide signals to the addressing valves, the number of switches equal to M+N;

wherein the plurality of switches are adapted to provide a number of signals equal to M+N to the addressing valves to individually control flow for each needle.

22. The tool of claim 21, wherein the plurality of switches are mounted to the tool body.

23. The tool of claim 21, wherein the plurality of switches includes M switches associated with M columns of needles, each of the M switches corresponding to and providing signals to valves for a corresponding column, and the plurality of switches further includes N switches associated with N rows of needles, each of the N switches corresponding to and providing signals to valves for a corresponding row.

24. The tool of claim 23, wherein the plurality of switches include fluid valves that provide at least one of a fluid pressure and a fluid flow to corresponding addressing valves.

25. The tool of claim 21, wherein the plurality of switches are adapted to provide signals to the addressing valves to simultaneously control flow for a plurality of needles.

26. A robotically manipulable material handling tool, comprising:

a tool body;

a plurality of needles mounted to the tool body in M columns and N rows, each of the needles constructed and arranged to remove material from a work area and deposit material on a work area;

a plurality of membrane valves, each membrane valve associated with a corresponding needle and controlling a flow for the needle to move the needle or cause fluid to move in the needle;

a plurality of control valves that provide fluid control signals to the membrane valves, each control valve associated with a corresponding column of needles and providing a fluid control signal to control the membrane valves corresponding to the column of needles between open and closed states; and a plurality of drive valves that provide fluid drive signals to the membrane valves, each drive valve associated with a corresponding row of needles and providing a fluid drive signal to move needles or cause fluid to move in needles in the corresponding row;

wherein the number of control and drive valves is equal to M+N, the number of signals from the control and drive valves is equal to M+N, and the control and drive valves are adapted to provide signals to the membrane valves to individually control one of movement of and flow in each needle.

* * * * *